(12) United States Patent
Adams et al.

(10) Patent No.: US 6,610,652 B2
(45) Date of Patent: *Aug. 26, 2003

(54) MICRODOSE THERAPY

(75) Inventors: Michael A. Adams, Kingston (CA); Jeremy P. W. Heaton, Gananoque (CA); James D. Banting, Kingston (CA)

(73) Assignee: Queen's University at Kingston, Kingston (CA)

( * ) Notice: Subject to any disclaimer, the term of this patent is extended or adjusted under 35 U.S.C. 154(b) by 53 days.

This patent is subject to a terminal disclaimer.

(21) Appl. No.: 10/095,654

(22) Filed: Mar. 8, 2002

(65) Prior Publication Data

US 2002/0091088 A1 Jul. 11, 2002

Related U.S. Application Data

(63) Continuation of application No. 09/613,637, filed on Jul. 11, 2000, now Pat. No. 6,423,683, which is a division of application No. 09/469,649, filed on Dec. 22, 1999, now Pat. No. 6,165,975, which is a continuation of application No. PCT/CA98/00603, filed on Jun. 22, 1998.
(60) Provisional application No. 60/086,750, filed on May 27, 1998, and provisional application No. 60/050,491, filed on Jun. 23, 1997.

(51) Int. Cl.$^7$ .................. A61K 38/00; A61K 31/43; A61K 31/535; A61K 31/34; A61K 31/195; A61K 31/13
(52) U.S. Cl. .................. 514/2; 514/192; 514/231.2; 514/470; 514/565; 514/668
(58) Field of Search .................. 514/2, 192, 231.2, 514/470, 565, 668

(56) References Cited

U.S. PATENT DOCUMENTS

| | | | |
|---|---|---|---|
| 4,421,737 A | * | 12/1983 | Ito et al. |
| 4,533,540 A | * | 8/1985 | Blank |
| 4,559,222 A | * | 12/1985 | Enscore et al. |
| 4,615,699 A | * | 10/1986 | Gale et al. |
| 4,654,209 A | * | 3/1987 | Leslie et al. |
| 4,655,766 A | * | 4/1987 | Theeuwes et al. |
| 4,681,584 A | * | 7/1987 | Gale et al. |
| 4,751,087 A | * | 6/1988 | Wick |
| 4,784,857 A | * | 11/1988 | LaBaw et al. |
| 5,071,656 A | * | 12/1991 | Lee et al. |
| 5,565,466 A | * | 10/1996 | Gioco et al. |
| 5,686,099 A | * | 11/1997 | Sablotsky et al. |
| 5,731,339 A | * | 3/1998 | Lowrey |
| 5,859,006 A | * | 1/1999 | Daugan |
| 5,877,216 A | * | 3/1999 | Place et al. |
| 6,024,976 A | * | 2/2000 | Miranda et al. |
| 6,165,975 A | * | 12/2000 | Adams et al. |
| 6,306,841 B1 | * | 10/2001 | Place et al. |

FOREIGN PATENT DOCUMENTS

| | | |
|---|---|---|
| WO | WO 95/19978 | 7/1995 |
| WO | WO 96/32003 | 10/1996 |
| WO | WO 96/38131 | 12/1996 |
| WO | WO 97/03985 | 2/1997 |

OTHER PUBLICATIONS

*3M Delivery*, "First CFC–free MDI Approved for Use in the United States," Oct. 1996; vol. 8:1–11, plus 4 pages of Supplemental Information provided herewith.
Puckett, K.L., et al., "Alternate Packaging Technology for Transdermal/Transmucosal Drug Delivery Systems," *3M Pharmaceuticals Study* (No Date Available).
Wick. S.M., "Developing A Drug–in–Adhesive Design for Transdermal Drug Delivery," *Adhesives Age*, Sep. 1995.
Wolff, H., "Optimal process design for the manufacture of transdermal drug delivery systems," *PSTT*, May 2000, vol. 3, No. 5; pp. 173–181.
Goldstein et al., "Oral Sildenafil in the Treatment of Erectile Dysfunction," *New England Journal of Medicine* 1998 338(20):1397–1404.
Webb et al., "Sildenafil Citrate and Blood–Pressure–Lowering Drugs: Results of Drug Interaction studies with an Organic Nitrate and a Calcium Antagonist," *Am. J. Cardiology* 1999 83(5A):21C–28C.
Maurice et al., "Molecular Basis of the Synergistic Inhibition of Platelet Function by Nitrovasodilators and Activators of Adenylate Cyclase: Inhibition of Cyclic AMP Breakdown by Cyclic AMP," *Molecular Pharm.* 1990 37:671–681.
Maurice et al., "Nitroprusside enhances isoprenaline–induced increases in cAMP in rat aortic smooth muscle," *Eur. J. Pharm.* 1990 191:471–475.

* cited by examiner

*Primary Examiner*—Raymond Henley, III
(74) *Attorney, Agent, or Firm*—Townsend and Townsend and Crew LLP

(57) ABSTRACT

Methods for treating vascular conditions associated with localized imbalance in vascular tone, which are hypothesized to be largely due to elevated endothelin (ET) are provided. The methods involve administration of nitric oxide (NO), agents which are able to provide NO, such as NO donors, agents which activate guanyl cyclase, such as YC-1, or agents which prolong the actions of endogenous NO or cyclic guanosine monophosphate (cGMP; a 2nd messenger molecule), such as phosphodiesterase (PDE) inhibitors. According to the invention, such agents are administered in minimal doses or microdoses by any route known in the art, so as to provide dosages which are about one half to about one twentieth ($\frac{1}{2}$ to $\frac{1}{20}$) of those known to induce vasodilation in "normal" circulations. The low doses of these agents effectively alleviate vascular conditions associated with a reduction in NO production or an attenuation of NO effect, by restoring balance in vascular tone while exerting almost no systemic effect in normal vasculature.

20 Claims, 8 Drawing Sheets

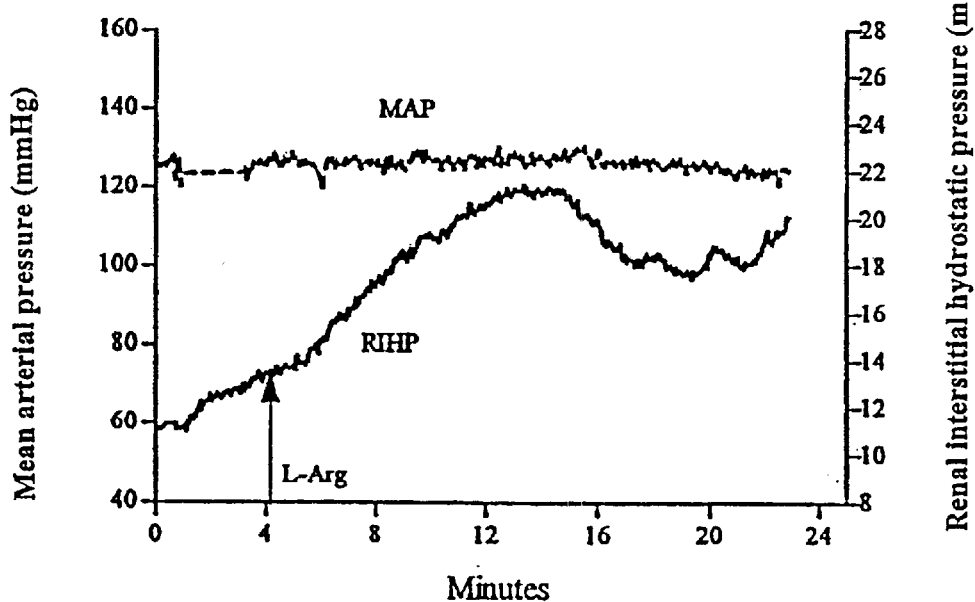
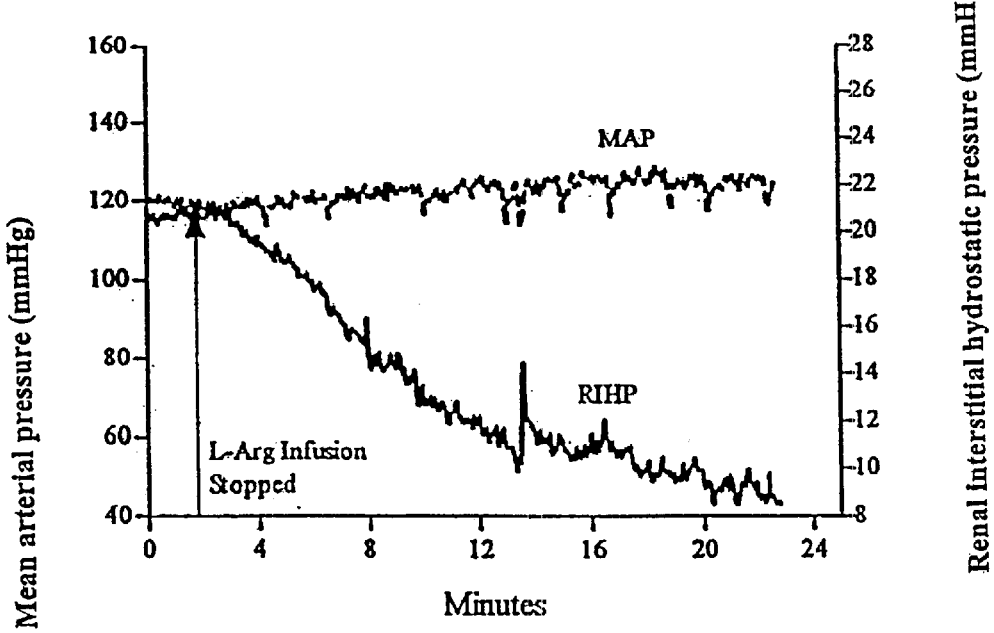

FIGURE 11
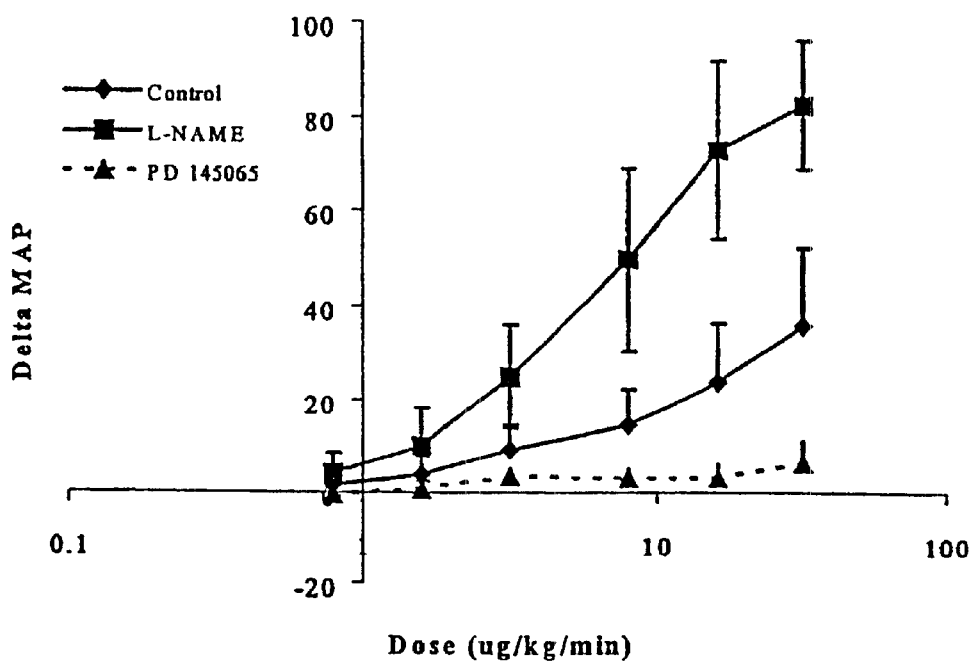
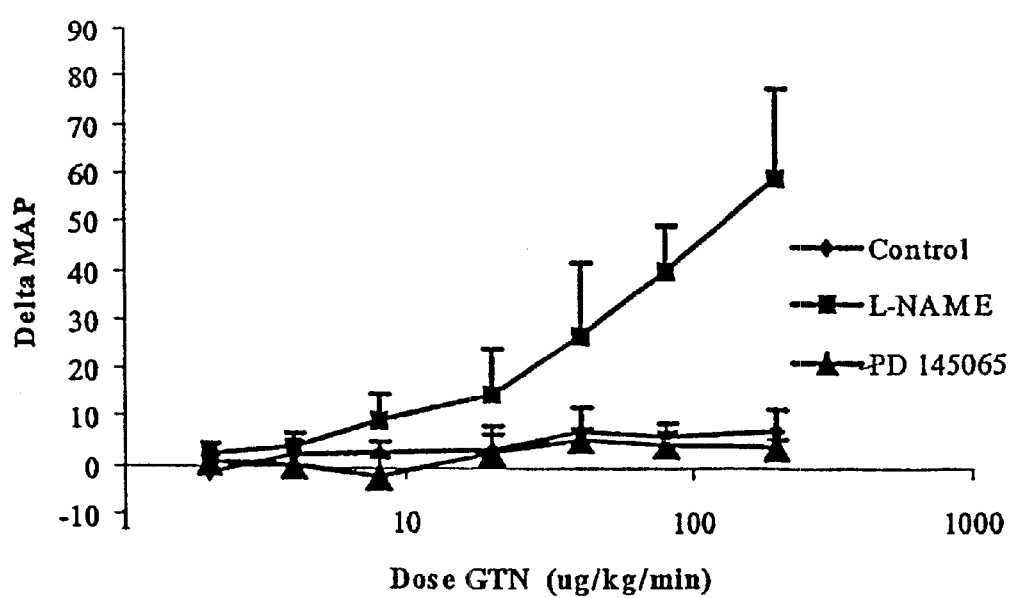

MICRODOSE THERAPY

RELATED APPLICATIONS

This application is a continuation of U.S. patent application Ser. No. 09/613,637, filed Jul. 11, 2000, now U.S. Pat. No. 6,423,683 which is Divisional Application of U.S. Application Ser. No. 09/469,649, filed Dec. 22, 1999, now U.S. Pat. No. 6,165,975, which is a continuation of PCT/CA98/00603, filed Jun. 22, 1998, and published as WO98/58633on Dec. 30, 1998, which application claims the benefit of priority of U.S. Provisional Patent Application Nos. 60/050,491, filed Jun. 23, 1997, and 60/086,750, filed May 27, 1998, the contents of all these applications are incorporated herein by reference in their entirety.

FIELD OF THE INVENTION

The field of invention is the treatment of conditions concerned with peripheral vasoconstriction. More particularly, the invention is concerned with methods for establishing normal vascular tone in regions of the circulation which demonstrate pathophysiology. In particular, the invention concerns a method of treating erectile dysfunction by provision of nitric oxide, nitric oxide producing agents, or activators of guanyl cyclase in small doses or microdoses, i.e., doses that do not induce undesirable side effects, such as systemic vasodilation, under normal conditions.

BACKGROUND OF THE INVENTION

It is widely known that administration of nitric oxide (NO), or compounds which deliver NO (i.e., NO donors, NO producing agents) to a subject, can provoke powerful vasodilator responses. Such administration is often accompanied by a number of undesirable side effects which include headache, flushing, and hypotension.

The physiological role of NO has been described as that of a powerful chronic vasodilator agent based on there being a marked increase in vascular tone following NO synthase (NOS) blockade (Johnson et al., Am. J. Hypertens. 5:919, 1992; Tolins et al., Hypertens. 17:909, 1991). The role of NO as a chronic vasodilator has only been inferred by indirect means, i.e., by removal of NOS activity. Endogenously, much more multiplicity and overlap in the control of vasodilation can be inferred from the scientific literature. For example, vasodilation can be induced by acetylcholine, bradykinin, adenosine, adenosine triphosphate (ATP), histamine, vasoactive intestinal polypeptide (VIP), and leukotrienes, amongst others. The actions of these endogenous modulators have been shown to be dependent, at least in part, on the presence of the endothelium, an effect likely mediated by endothelial derived relaxing factor/NO (EDRF/NO) (Garg, U. C. et al., J. Biol. Chem. 266:9, 1991; Garg, U. C. et al., J. Clin. Invest. 83:1774, 1989; Palmer, R. M. J. et al., Nature 327:524, 1987). Other vasodilator mechanisms exist which are not endothelium dependent, such as $\beta_2$-adrenergic receptor activation, atrial natriuretic peptide (ANP) and certain prostaglandins. The actions of NO have been suggested to be mostly cGMP-mediated via guanylate cyclase activation, although other mechanisms have been suggested. For example, Garg et al. (J. Biol. Chem. 266:9, 1991; J. Clin. Invest. 83:1774, 1989) and others (Assender, J. W. et al., J. Cardiovasc. Pharmacol. 17(Suppl.3):S104, 1991; O'Conner, K. J. et al., J. Cardiovasc. Pharmacol. 17(Suppl.3):S100–S103, 1991) demonstrated a difference in the effects of NO-generating vasodilator agents in inhibiting vascular smooth muscle cell growth in culture; however, it is clear that NO can act not only as a vasodilator but also to inhibit vascular growth responses in a number of conditions (Farhy, R. D. et al., Circ. Res. 72:1202, 1993).

It has been believed and widely practised that NO, in humans and animals, produced via sodium nitroprusside (SNP) infusion, causes vasodilation in peripheral vasculature at doses greater than 10 $\mu$g/kg per min. It has recently been determined that NO also performs a function through interaction with endothelin (ET) (Banting et al., J. Hypertens. 14:975, 1996; Richard et al., Circulation 91:771, 1995). Prior to this time, ET had been believed to play a minimal role in maintaining tone in the peripheral microvasculature and to have little impact on the state of contraction of smooth muscle in those vessels. Recent studies have indicated (Banting et al., J. Hypertens. 14:975, 1996) that ET is under the inhibitory control of NO and that administration of NOS inhibitors results in elevated levels of ET.

Endothelins were first described in 1988 and have been shown to be powerful vasoconstrictors, predominantly found in vascular endothelium and, since that time, numerous ET antagonists and their pharmaceutically acceptable salts have been identified and can be obtained commercially (e.g., Sigma, American Peptides). Detailed descriptions of the chemical structures of various ET antagonists may be found in U.S. Pat. No. 5,284,828 issued Feb. 8, 1994 to Hemmi et al., U.S. Pat. No. 5,378,715 issued Jan. 3, 1995 to Stein et al., and U.S. Pat. No. 5,382,569 issued Jan. 17, 1995 to Cody et al. In addition, U.S. Pat. No. 5,338,726 issued Aug. 16, 1994 to Shinosaki et al. describes the chemical structure of ET converting enzyme inhibitors. To date, however, antagonists of ET have not been approved for therapeutic use, although a number of investigators have postulated that ET antagonists could be used for conditions ranging from renal failure, endotoxic shock, asthma, angina, or diabetes to pulmonary hypertension and possibly other indications.

Under normal physiological conditions, ET can be found in almost all parts of circulation at very low levels. In general, in the normal rodent circulation ET is not found in elevated quantities and appears to have little detectable role in the normal regulation of vascular tone, i.e., there is no appreciable decrease in blood pressure when an ET antagonist is administered by injection in normal circulation. Further, at present there does not appear to be any evidence suggesting that ET plays a physiological role even in a small portion of the circulation under normal circulatory conditions in experimental models. However, it is likely that the systemic circulation may appear to be normal when, in fact, specific regions of the circulation are undergoing pathophysiological changes such as occurs in conditions such as erectile dysfunction (ED) (Adams et al., Int. J. Impot. Res. 9:85–91, 1997).

Consequently, there are cardiovascular conditions which are traditionally treated in human beings by significant doses of NO or NO donors, such as glyceryl trinitrate (GTN) (0.2 mg/h and greater). However, these doses are known to induce systemic vasodilation and provoke considerable overall systemic side effects (The, L. S. et al., Brit. J. Rheum. 34:636, 1995). This is particularly so where a pathological condition exists only in certain major organs (e.g., heart, kidney, liver). As a result, a satisfactory method for promoting recovery of normal perfusion pressure in organs with certain pathologies without producing overall systemic hypotension has not been discovered.

Based on the understanding that a significant portion of underlying problems in clinical erectile dysfunction relates to "vascular" mechanisms, much of the current state-of-the-art research involves determining the contribution that the different vascular effector control systems make in normal and pathophysiological states. There is substantial understanding of hemodynamic events that lead to an erection, and yet the quantitative roles of each of the neuroeffector, humoral and local systems in these events remain poorly described. Since 1990, NO has been considered the primary non-adrenergic non-cholinergic neurotransmitter in the penis and has been presumed to be the primary mediator of corporal relaxation during erection (Ignarro L. J. et al., *Biochem. Biophys. Res. Comm.*, 170:843, 1990).

It is well established that, for an erection to occur, neurally mediated (autonomic) vasodilation of the penile arterial blood vessel and the trabecular meshwork takes place (Lue, T. F. et al., *J. Urol.* 137(5):829, 1987) permitting increased blood flow into the cavernous bodies of the penis. The expanding intra corporal volume compresses the effluent veins that lie between the erectile tissue and the surrounding fibrous, relatively inelastic, tunica albuginea. The outflow capacity is thereby decreased and entrapment of blood ensues, resulting in the transformation of the flaccid penis into its erect state (Lue, T. F. et al, *J. Urol.* 137(5):829, 1987; Juenemann, K. P. et al., *J. Urol.* 136(1):158, 1986; Lue, T. F. et al.,*J. Urol.* 130:1237, 1983; Weiss, H. et al.,*Ann Intern. Med.* 76:793, 1980). The level of arterial vascular tone (i.e., blood pressure) is one of critical importance in this process, although adequate perfusion pressure is also a necessary factor. The converse, detumescence, is mediated by the sympathetic nervous system (Saenz de Tajada, I. et al., *Am. J. Physiol.* 254:H459, 1988; Juenemann, K. P. et al., *Br.J. Urol.* 64, 1989).

The issue of "impotence" (defined as "a pattern of persistent or recurrent inability to develop or maintain an erection of sufficient rigidity for successful coitus") was discussed at a consensus conference of the National Institutes of Health (NIH) in Washington in December 1992 and has been clearly identified as having a wide range of causative or associated factors. The Massachusetts Male Aging Study (MMAS) has provided an updated view of the epidemiology of erectile dysfunction. It is accepted that the prevalence of impotence increases with age (Kinsey A. C. et al., "Sexual Behaviour in the Human Male", W. B. Saunders: Philadelphia, 1948). Severe or complete ED increases from 5 to 15% between 40 and 70 years of age, (Feldman, H. A. et al., *J. Urol.* 151:54, 1994). ED has been shown to be "directly correlated with heart disease, hypertension, diabetes, associated medications, indices of anger and depression, and inversely with serum dehydroepiandrosterone, high density lipoprotein, cholesterol and an index of dominant personality."

It is now estimated that in North America there are more than 30,000,000 men with some form of ED, a significant increase from the figure of 10,000,000 quoted just 10 years ago (Shabsigh, R. et al., *Urology* 32:83, 1988; Whitehead E., *Geriatrics* 43(2):114, 1988; Furlow, W. L. et al., *Med. Aspects Human Sexuality* 19:13, 1985). From these figures it is also reasonable to estimate that as many as three million Canadian men may have a degree of ED. The direct cost of treating impotence is significant. Reliable figures from 1985 show that the cost of treating impotence exceeded 146 million dollars in the United States in that year alone (National Center for Health Statistics) and this number is just the estimated market size for one type of injectable therapy. The secondary effects and indirect costs associated with ED suggest that impotence and sexual dysfunction are medical icebergs. The consequences of sexual dysfunction may be seen in strains on the host relationship potentially leading to marital breakdown, violence, work related sequelae, deviant sexual behaviour and impacts on children, when present, that can carry the damage into a new generation of unwanted behaviours. If ED underlies even a small but significant percentage of marital and family breakdown, then it adds vastly to the social and economic burden in society. The pragmatic issue is that large numbers of men are now being treated for ED and most of the treatments are fairly blunt instruments (e.g., intracavernosal injection (ICI)) of mixed vasoactive compounds, penile prosthesis insertion) with significant cost and complications (ICI: pain, priapism, dislike of the technique; prostheses: reoperation, infection, distortion of body image).

Administration of NO, or compounds which are able to deliver NO, have been suggested as possible therapies; however, these agents can provoke powerful yet inappropriate vasodilator responses (Brock et al., *J. Urol.* 150:864, 1993). Such administration is often accompanied by a number of undesirable side effects related to systemic vasodilation which include headache, flushing, and hypotension. Consequently, there is a real need to provide methods whereby ED and other vascular disease may be quickly and effectively treated without any inappropriate side effects.

SUMMARY OF THE INVENTION

Problems associated with localized imbalance in vascular tone, such as seen in ED, and which are hypothesized to be largely due to elevated ET, may be relieved by the administration of agents which are able to provide NO, by direct administration of NO, or by administration of an agent or agents which activates guanyl cyclase, such as, for example, YC-1, or other agents which prolong the actions of endogenous NO or of cGMP (a 2nd messenger molecule), such as phosphodiesterase (PDE) inhibitors, in minimal doses or microdoses, which heretofore had not been thought to result in effective treatment of an imbalance in vascular tone.

In the normal physiological state, there are sufficient quantities of NO present in the vasculature to maintain appropriate levels of ET (Banting et al., *J. Hypertens.* 14:975, 1996). The addition of further NO has little impact on the effect of ET and consequently any further vasodilation seen in such normal smooth muscle in the vasculature is likely attributable to NO's effects on the generation of cGMP, with cGMP resulting in decreased levels of $Ca^{++}$. In certain pathological conditions, such as diabetes and cardiovascular disease, and/or as a consequence of age, tissue is unable to provide satisfactory levels of NO in order to suppress normal levels of ET present in smooth muscle tissues.

As such, physiological conditions where NO production is reduced in a specific local circulation, such as male ED, indicate that suppression of ET activity should offer an effective treatment. Consequently, in accordance with this, the present invention provides for the use of an agent or agents which directly or indirectly generates NO at dosages which are about one half to about one twentieth ($\frac{1}{2}$ to $\frac{1}{20}$) of those known to induce vasodilation in "normal" circulations, and consequently exert almost no effect in the normal vasculature. As such these low doses, or "microdoses" are hypothesized to normalize the balance between NO and ET. The range of about $\frac{1}{2}$ to about $\frac{1}{20}$ is derived from the observation that at doses which are below about $\frac{1}{2}$ the normal dose, systemic effects are generally no longer seen. At about $\frac{1}{20}$ the normal dose, however, the desired effect is also generally no longer observed, i.e., there is no effect.

According to one aspect of the present invention the concept of "low-dose" agents which directly or indirectly generate NO, or prolong the action of NO, or enhance the cGMP 2nd messenger system, such as PDE inhibitors, is also applicable to any other peripheral pathological conditions where, regardless of the origin, NO is at least partially inhibited.

According to a further aspect of the present invention, there is provided a method for restoring normal vascular tone in vasculature where NO levels are depleted and restoration of such levels may be achieved by addition of NO at levels which do not appreciably alter normal systemic vascular tone.

According to yet a further aspect of the present invention there is provided a method to treat any condition where NO levels are at least partially inhibited or reduced, wherein the method comprises administration of NO or one or more NO donors, or one or more agents which activate guanyl cyclase, by oral, sublingual, buccal, intravenous, transdermal, or any other effective route, in concentrations that are about ½ to about 1/20 of a concentration required to induce vasodilation in "healthy" or normal regions such as the coronary or skeletal muscle vasculature. Preferably, the concentrations of the method of the present invention are about one quarter to about one twentieth (¼ to 1/20) of a concentration required to induce vasodilation in "healthy" or normal regions such as the coronary or skeletal muscle vasculature. Still more preferably, the concentrations of the method of the present invention are about one eighth to about one sixteenth (⅛ to 1/16) of a concentration required to induce vasodilation in "healthy" or normal regions such as the coronary or skeletal muscle vasculature.

According to one aspect of the present invention there is provided a method to treat instances of renal disease associated with excessive vasoconstriction where NO levels are at least partially inhibited, wherein the method comprises administration of NO or one or more NO donors, or one or more agents which activate guanyl cyclase, by oral, sublingual, buccal, intravenous, transdermal, or any other effective route, in concentrations that are about ½ to about 1/20 of a concentration required to induce vasodilation in "healthy" or normal regions of the circulation such as the coronary or skeletal muscle vasculature.

According to a another aspect of the present invention there is provided a method to treat premature aging of the skin associated with inappropriate vasoconstriction of the skin vasculature which is associated with at least partial inhibition of NO levels in the skin, wherein the method comprises administration of NO or one or more NO donors, or one or more agents which activate guanyl cyclase, by oral, sublingual, buccal, intravenous, transdermal, or any other effective route, in concentrations that are about ½ to about 1/20 of a concentration required to induce vasodilation in "healthy" or normal regions such as the coronary or skeletal muscle vasculature.

According to a further aspect of the present invention there is provided a method to treat male ED caused at least by partial inhibition of NO in the penile vasculature wherein the method comprises administration of NO or one or more No donors, or one or more agents which activate guanyl cyclase, by oral, sublingual, buccal, intravenous, transdermal, or any other effective route, in concentrations that are about ½ to about 1/20 of a concentration required to induce vasodilation in "healthy" or normal regions such as the coronary or skeletal muscle vasculature.

According to yet a further aspect of the present invention there is provided a method to treat ED comprising administering to a subject in need thereof a quantity of glyceryl trinitrate (GTN) by any route, for example, oral, sublingual, transdermal, intravenous, or inhalation, that provides plasma concentrations of below about 250 pg/ml of the GTN, so that ED is treated.

According to one aspect of the present invention there is provided a low-dose transdermal "patch" with short term release of, for example, GTN or any other effective provider of NO, such as, for example, one or more NO donors or one or more agents which activate guanyl cyclase, over a period of time less than 6 hours (as opposed to 12, 18 or 24 hour release), which restores normal vascular tone in an affected local vascular bed, such as the pudendal or penile vasculature of men with ED, without inappropriately affecting systemic vascular tone or causing hypotension, and preferably, but not necessarily, without inducing tolerance (Bennett et al., *Circ. Res.* 63:693, 1988) to the effects and/or biotransformation of a NO releasing compound to its releasing form.

According to a further aspect of the present invention, there is provided a low dose or microdose "patch" with long term release of, for example, GTN, or any other effective provider of NO, such as, for example, one or more NO donors, or one or more agents which activate guanyl cyclase, over a period of time greater than 6 hours (typically 12 to 24 hour release), which restores normal vascular tone in an affected local vascular bed, such as the pudendal or penile vasculature of men with ED, without inappropriately affecting systemic vascular tone, and preferably, but not necessarily, without inducing tolerance to the effects of a NO releasing compound and/or biotransformation of a NO releasing compound to its releasing form.

According to a further aspect of the present invention there is provided a method to treat female sexual dysfunction (SD) wherein the method comprises administration of NO or one or more NO donors, or one or more agents which activate guanyl cyclase, by oral, sublingual, buccal, intravenous, transdermal, or any other effective route, in concentrations that are about ½ to about 1/20 of a concentration required to induce vasodilation in "healthy" or normal regions such as the coronary or skeletal muscle vasculature.

According to yet a further aspect of the present invention there is provided a method to treat SD comprising administering to a subject in need thereof a quantity of GTN by any route, for example, oral, sublingual, transdermal, intravenous, or inhalation, that provides plasma concentrations of below about 250 pg/ml of the GTN, so that SD is treated.

According to one aspect of the present invention there is provided a low-dose transdermal "patch" with short term release of, for example, GTN, or any other effective provider of NO such as, for example, one or more NO donors or one or more agents which activate guanyl cyclase, over a period of time less than 6 hours (as opposed to 12, 18 or 24 hour release), which restores normal vascular tone in an affected local vascular bed, such as the pudendal, cervical or vaginal vasculature of women with SD, without inappropriately affecting systemic vascular tone or causing hypotension, and preferably, but not necessarily, without inducing tolerance (Bennett et al., *Circ. Res.* 63:693, 1988) to the effects and/or biotransformation of a NO releasing compound to its releasing form.

According to a further aspect of the present invention there is provided a low dose or microdose "patch" with long term release of, for example, GTN, or any other effective provider of NO, such as, for example, one or more NO donors or one or more agents which activate guanyl cyclase, over a period of time greater than 6 hours (typically 12 to 30 hour release), which restores normal vascular tone in an affected local vascular bed such as the pudendal, cervical or vaginal vasculature of women with SD without inappropriately affecting systemic vascular tone, nor inducing tolerance to the effects of a NO releasing compound and/or biotransformation of a NO releasing compound to its releasing form.

| Definitions | |
|---|---|
| GTN | glyceryl trinitrate |
| ISMN | isosorbide 5-mononitrate |
| ISDN | isosorbide dinitrate |
| PETN | pentaerythritol tetranitrate |
| ETN | erythrityl tetranitrate |
| SNP | sodium nitroprusside |
| SIN-1 | 3-morpholinosydnonimine molsidomine |
| SNAP | S-nitroso-N-acetylpenicillamine |
| SNOG | S-nitrosoglutathione |
| NOHA | N-hydroxy-L-arginine |
| cAMP | cyclic adenosine monophosphate |
| cGMP | cyclic guanosine monophosphate |
| L-NAME | $N^\omega$ nitro-L-arginine methyl ester |
| $IP_3$ | inositol-1,4,5-triphosphate |
| RIHP | renal interstitial hydrostatic pressure |
| T | tumescence |
| R | rigidity |

"Applying various forms of NO" as used herein includes administering NO donor or NO producing agents.

"Enhancing penile erection" as used herein is understood to mean increasing physical size and improving tumescence and/or rigidity of a penis, preferably so that it is capable of intromission.

"Erection of good quality" and "effective erection" are used herein interchangeably to mean adequate for vaginal penetration (i.e., intromission, or intercourse).

"NO donor", "NO producing agent", "NO delivering compound", "NO generating agent" and "NO provider" are used interchangeably in this specification and include all compounds which donate NO through biotransformation, compounds which generate NO spontaneously, compounds which spontaneously release NO, or any other compounds which otherwise generate NO or an NO-like moiety and include: glyceryl trinitrate, isosorbide 5-mononitrate, isosorbide dinitrate, pentaerythritol tetranitrate, erythrityl tetranitrate, sodium nitroprusside, 3-morpholinosydnonimine molsidomine, S-nitroso-N-acetylpenicillamine, S-nitrosoglutathione, N-hydroxy-L-arginine, S,S-dinitrosodithiol, or NO gas, or a functional equivalents thereof. In some cases, NO is generated by activation of guanyl cyclase.

"Penis" as used herein may be interpreted to apply equally to clitoris in so far as there is substantial equivalence between penile and clitoral erectile tissue. "Sexual dysfunction" (SD) as used herein includes aspects of female dysfunction and urogenital aging such as decreased vaginal lubrication, decreased vaginal engorgement, pain during intercourse such as, for example, dyspareunia, urogenital infections; and urogenitalia as affected by post-menopause, diabetes, vascular disease, estrogen depletion conditions, sexual dysfunction, and idiosyncratic vaginal dryness, respectively.

"Various forms of NO" as used herein is understood to mean any one of $NO^\cdot$, $NO^+$ and $NO^-$, preferably $NO^+$ and $NO^-$, and can include as an alternative CO (carbon monoxide) in its various forms, which produces an equivalent effect to NO.

"Without inappropriately affecting systemic vascular tone" as used herein means not affecting mean arterial pressure so as to produce inappropriate systemic vasodilation with effects such as hypotension, headache, flushing.

BRIEF DESCRIPTION OF THE DRAWINGS

Embodiments of the invention will now be described, by way of example, with reference to the accompanying drawings, wherein:

FIG. 6 is a representative tracing of changes in mean arterial pressure and renal interstitial hydrostatic pressure (RIHP) in respect of the capacity of L-arginine to induce decreases in RIHP in connection with the renal circulation.

FIG. 7 is a representative tracing of changes in mean arterial pressure and renal interstitial hydrostatic pressure (RIHP) in respect of decreasing RIHP following removal of L-arginine in the renal circulation.

FIGS. 11 and 12 are graphs illustrating a dose-response relationship of mean arterial pressure for different doses of the nitric oxide donors SNP (top panel) and GTN (bottom panel), before and after both nitric oxide synthase blockade (L-NAME) and endothelin receptor antagonism (PD145065).

DETAILED DESCRIPTION OF THE INVENTION

The physiological role of NO has been described as that of a chronic vasodilator agent acting to persistently "offset" the actions of a number of vasoconstriction systems. However, as discussed by Banting et al. (J. Hypertens.

14:975, 1996), based on this rationale, this would reveal that the NO vasodilator system would normally have an overall activity level at close to 70% of the NO system's maximal capacity, leaving the system little reserve or gain to protect against further deviations in mean arterial pressure and blood flow homeostasis.

Banting et al. (*J. Hypertens.* 14:975, 1996) proposed that the chronic role of NO, in vivo, is not that of a chronic vasodilator system but rather an inhibitor of the activity of local vasoconstrictor agents, such as ET. That is, the hypertension following blockade of NO production was completely reversed with the administration of an ET receptor antagonist. This finding, combined with the understanding that ET appears to play almost no role in the "normal" physiological control of resting mean arterial pressure, indicates that the function of NO may be different than previously proposed. The results of the Quantitative Study as detailed below, in summary, indicate that:

(i) the amount of NO required to completely restore mean arterial pressure in L-NAME treated rats from hypertensive levels is much less than that required to lower mean arterial pressure under control conditions;

(ii) the increase in sensitivity to NO and NO donors allows for as little as 1/20th of the standard concentration to provide a given vasodilator response in NO synthase blockade rats;

(iii) the level of NO required to completely reverse the hypertension in the chronic phase of L-NAME induced hypertension without altering blood pressure in control rats is at the same level as required to reverse the hypertension following acute NO synthase blockade; and (iv) the similar mean arterial pressure lowering, in both treated and control rats, that occurred with the administration of "high" concentrations of sodium nitroprusside suggests that signalling processes have been "normalized" at approximately 10–12 ug/kg per minute of sodium nitroprusside infusion.

Figure 4:
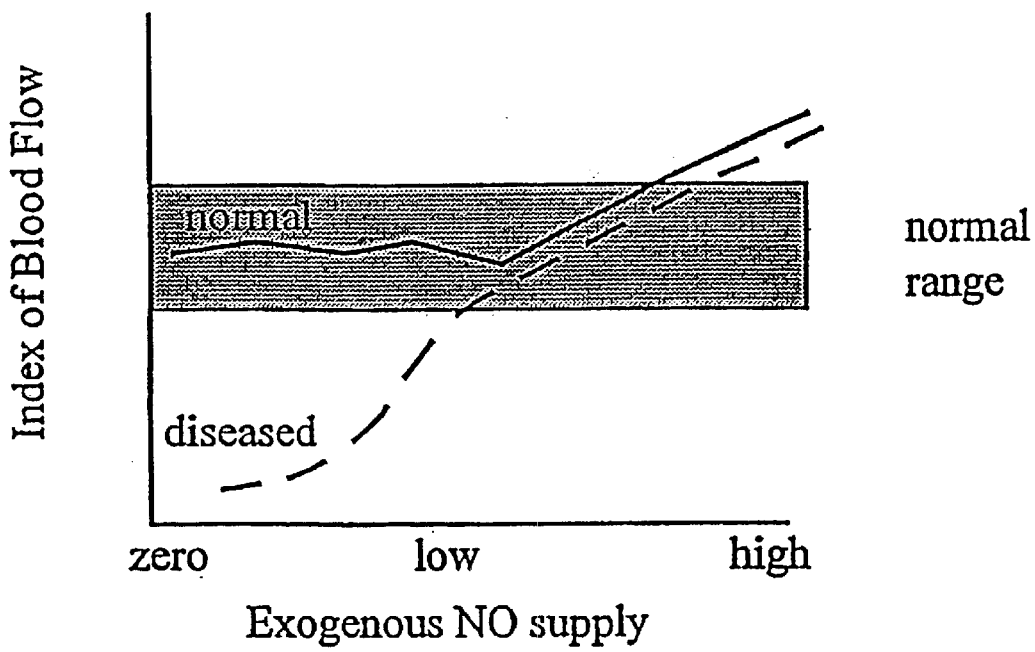
FIG. 4 is a schematic diagram depicting a range representative of a "normal" vascular controlling "window" of NO with comparisons of control and L-NAME treated rats.

Banting et al. (*J. Hypertens.* 14:975, 1996) have suggested that a major role of NO is not to function as a chronic vasodilator, but rather a chronic inhibitory regulator of ET-mediated vasoconstriction. In that study it was demonstrated that ET-mediated vasoconstriction does not contribute to the maintenance of vascular tone in a circulation with an intact NO generating system. Also, it was demonstrated that almost the entire L-NAME induced hypertension was both prevented and/or reversed via the administration of an ET receptor antagonist. The results detailed below under the heading Quantitative Study quantitate the exogenous level of NO required to restore this regulatory balance and, taken together, we propose that NO functions to suppress ET-mediated vasoconstriction within a physiological "window" as illustrated in FIG. 4, in a manner which is unrelated to its direct role as a vasodilator substance. Indeed, it is proposed that the mechanism of action of the NO donors delivered at the micro doses disclosed herein, are not vasodilatory; rather they act to suppress the endogenous role of endothelin.

These conclusions and their applicability to other microcirculations are supported by studies conducted in the kidney in connection with measurements of renal interstitial hydrostatic pressure and mean arterial pressure as reported below under the heading: Effect of NO in Renal Vasculature.

In a further application of the present invention, studies conducted in human males with a low-dose "patch" with up to 3 hours of release of effective NO, demonstrate that providing a "microdose" of NO restored normal erectile function. The results of these studies are detailed below under the heading: Clinical Data: For erectile dysfunction reversal with microdoses of NO.

Accordingly, the present invention provides a method for restoring normal vascular tone through the use of an agent or agents which directly or indirectly generate(s) NO at dosages of about ½ to about 1/20 of those currently used in clinical applications.

The method of the present invention is also applicable to any other peripheral pathological conditions where regardless of the origin, NO is at least partially inhibited. In respect of the conditions detailed below evidence in the literature demonstrates that the production of NO is, at least partially, inhibited. This leads to an imbalance between NO and ET in favour of ET. The method of the present invention restores this balance with 'quantities' of NO that do not induce vasodilation, or not appreciably, in 'healthy' or non-NO deficient circulations. Conditions wherein the present invention has application include any condition where regional circulation exhibits inappropriate vasoconstriction, such as, for example, ED, conditions associated with female sexual dysfunction involving vaginal and/or pelvic circulation, Raynaud's phenomenon (a condition of the fingers with constrained blood flow), as well as conditions associated with inappropriate vasoconstriction in, for example, cutaneous and/or dermal (for example in reconstructive surgery, as well as scleroderma and diffuse cutaneous systemic sclerosis), cerebral, and renal circulations. Concerning ED, the therapy of the present invention can be used to restore "normal" vasculature response in a patient who has undergone a radical prostatectomy procedure where normal circulatory control may not return for 6–8 months post operatively.

The therapy of the present invention therefore has application in female dysfunction and urogenital aging conditions such as vaginal lubrication, vaginal engorgement, pain during intercourse (dyspareunia), urogenital infections; and urogenitalia as affected by post-menopause, diabetes, vascular disease, estrogen depletion conditions, sexual dysfunction, and idiosyncratic vaginal dryness, respectively. In such situations, the therapy of the present invention works to improve blood flow to the vagina leading to vaginal engorgement promoting better circulation (lubrication).

It is understood that any agent which provides a dose range of NO is intended to be included within the scope of the present invention. Thus, in accordance with the invention, an agent may be NO, an NO-like substance, a substance which directly releases NO (e.g., an NO donor) or causes the release of NO, a substance having NO-like activity or effect, a substance which directly activates guanyl cyclase, or a substance that prolongs the actions of the 2nd messenger molecule cGMP, such as a PDE inhibitor. Regardless of which of such agent or agents is employed in the methods of the invention, what is important is that an enhanced level of NO is achieved, or the effect of an enhanced level of NO is achieved. The enhanced level is delivered to the vasculature such that normal vascular tone is achieved by a mechanism which involves normalizing levels of ET, thereby restoring the tone of the target microvasculature.

It should also be understood that the methods of the invention include the administration of an agent or agents as described above, (i.e, NO, an NO-like substance, a substance which directly releases NO (e.g., an NO donor) or causes the release of NO, a substance having NO-like activity or effect, or a substance which directly activates guanyl cyclase), either acutely or chronically. Acute administration is administration of a finite duration and can be, for example, as short as that associated with treatment of ED, wherein administration takes place for a prescribed period of time (e.g., up to several hours) at discrete instances when the affect of the administration (penile erection) is desired. Acute administration can also be of longer, finite duration. Chronic administration is administration of a continuous and indefinite duration, and can be, for example, administration associated with a chronic condition such as that involving inappropriate vasoconstriction of the renal vasculature, where chronic administration is necessary to restore normal renal function.

The methods of the present invention are also applicable to treating vascular conditions wherein there is no appreciable decrease or inhibition of endogenous NO. Such vascular conditions occur, for example, when endothelial cells experience high shear from rapid movement of red blood cells passing in contact with, or in close proximity to, endothelial cells, resulting in increased ET. The methods of the invention restore NO/ET balance. High shear is associated with, for example, drug therapy and atherosclerosis.

While the invention has been particularly shown and described with reference to certain embodiments, it will be understood by those skilled in the art that various other changes in form and detail may be made without departing from the spirit and scope of the invention.

All scientific papers and patents referred to in this specification are incorporated in totality by reference herein.

Quantitative Study

Figure 1:
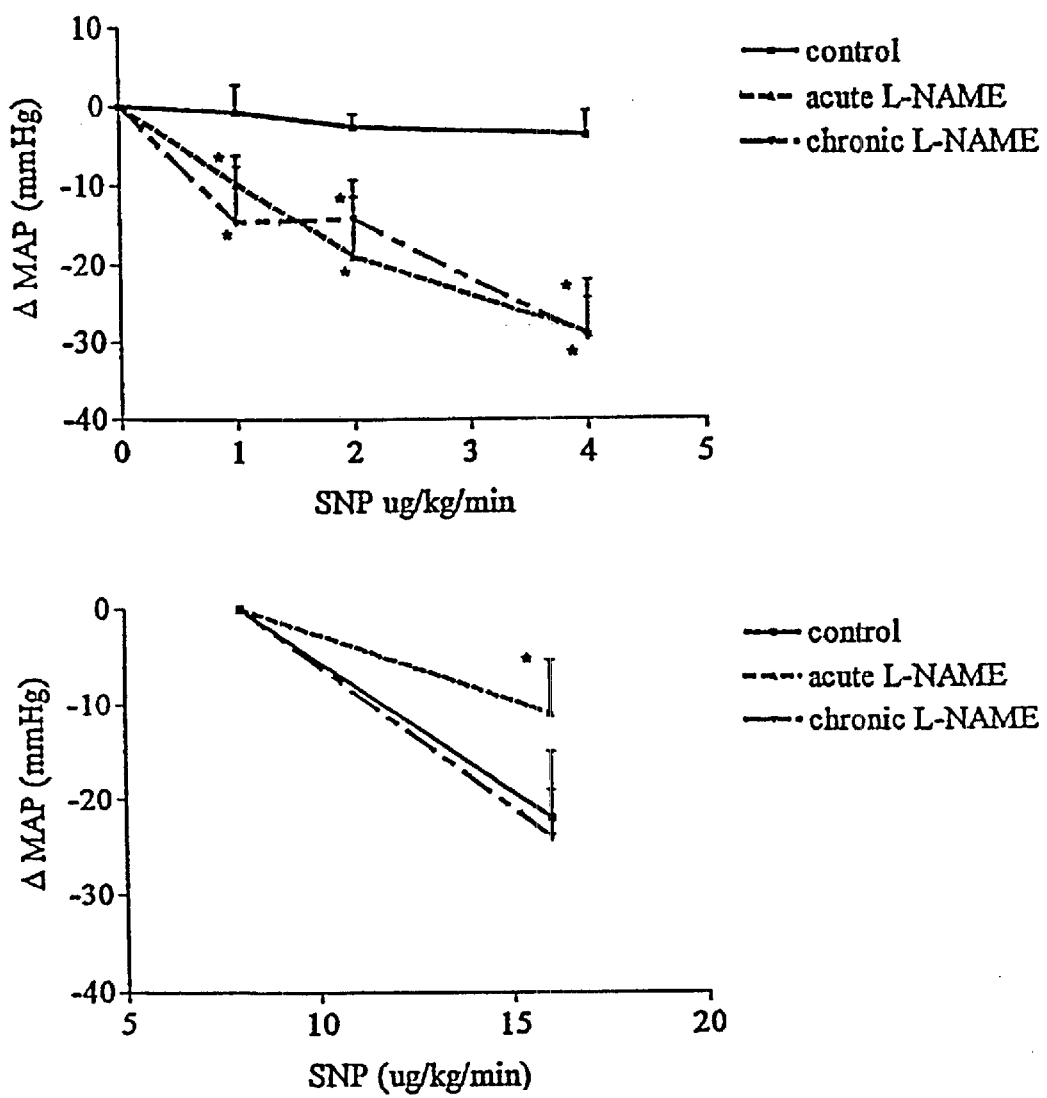
FIG. 1 is a graphical representation of results from measurements of mean arterial blood pressure in rats and illustrates the differential impact on mean arterial pressure (mmHg) of infusions of sodium nitroprusside in control and L-NAME treated rats.

The study detailed herein quantitatively characterizes the level of exogenous NO required to restore 'normal' vascular function following the acute and chronic blockade of NO synthase. Referring to the Figures, and in particular FIG. 1, the concentration-response relationship with increasing levels of sodium nitroprusside (SNP) is markedly shifted for both acute and chronic NO synthase blockade treated rats. The concentration-mean arterial pressure response curves were divided into two groups, concentrations that did not and those that did induce a lowering of mean arterial pressure in the controls. A similar increased sensitivity to low levels of SNP in the L-NAME treated rats was demonstrated both in acute and chronic phases of NO synthase blockade treatment. This level of SNP administration (0.5 to 8 ug/kg per minute) did not significantly decrease mean arterial pressure in control rats but did result in a marked decrease in mean arterial pressure.

Figure 2:
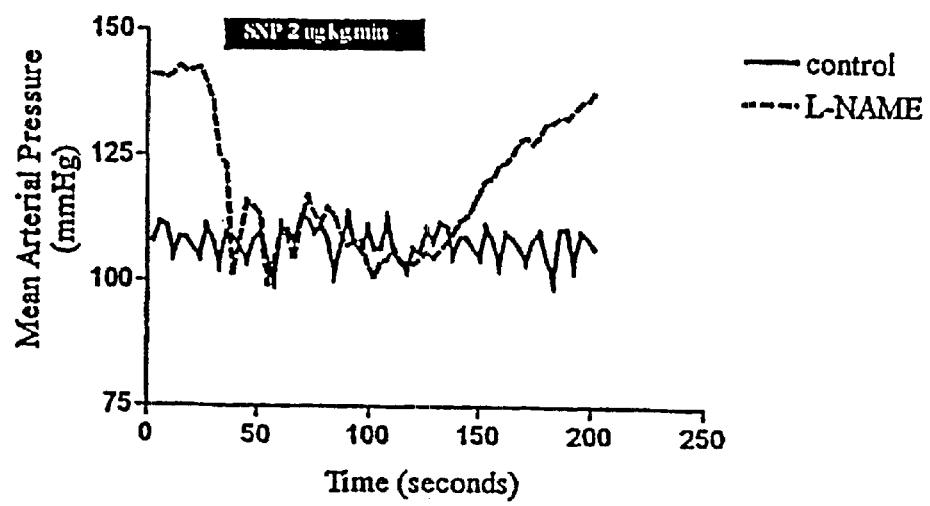
FIG. 2 is a representative tracing of measured mean arterial pressure in a rat demonstrating the contrasting effect of low level infusions of sodium nitroprusside in control and acute L-NAME treated rats.

Referring now to FIG. 2 there may be seen an illustrative example of this finding: the depressor response to 2 ug/kg per minute in the NO synthase blockade phase was superimposed over the 2 ug/kg per minute response in the control period. The mean arterial pressure lowering induced by 12–32 ug/kg per minute induced a similar lowering in both control and treated rats (see FIG. 1, lower panel), indicating a convergence with respect to the depressor response to SNP.

Figure 3:
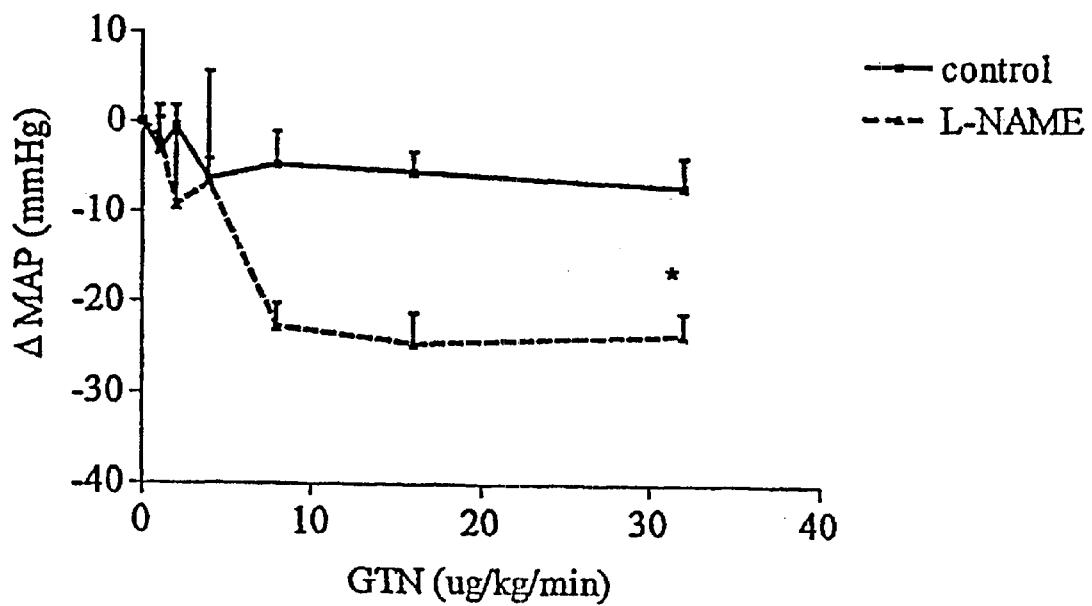
FIG. 3 is a graphical representation of measurements of mean arterial blood pressure illustrating an enhanced glyceryl trinitrate dose response curve in rats treated with control and L-NAME, acutely.

Referring now to FIG. 3 it may be seen that the cumulative glyceryl trinitrate concentration-mean arterial pressure response demonstrated results similar to SNP. The cumulative concentration-mean arterial pressure response curve was also shifted leftward in the NO synthase blockade treated rats. Again, the similar trend of concentrations that do not lower mean arterial pressure in the controls, almost completely reversed the NO synthase blockade induced hypertension.

Further studies assessed the impact of different vasoactive systems on the relationship between nitric oxide and endothelin and, more specifically, the low dose effects of nitric oxide and the suppression of local levels of endothelin (ET), which cause vasodilation and a normalization of vascular tone in focal regions of the circulation that are, at least in part, NO deficient. In these studies, L-NAME was administered to increase blood pressure, and two other vasodilator agents were employed: isopropylnorepinephrine (INE, a $B_1/B_2$ agonist, see FIG. 8) and the $\alpha_1$ blocker prazosin (see FIG. 9). INE activates a cAMP mediated signal transduction system, and prazosin decreases the activity of an $IP_3$ signal transduction system.

Figure 8:
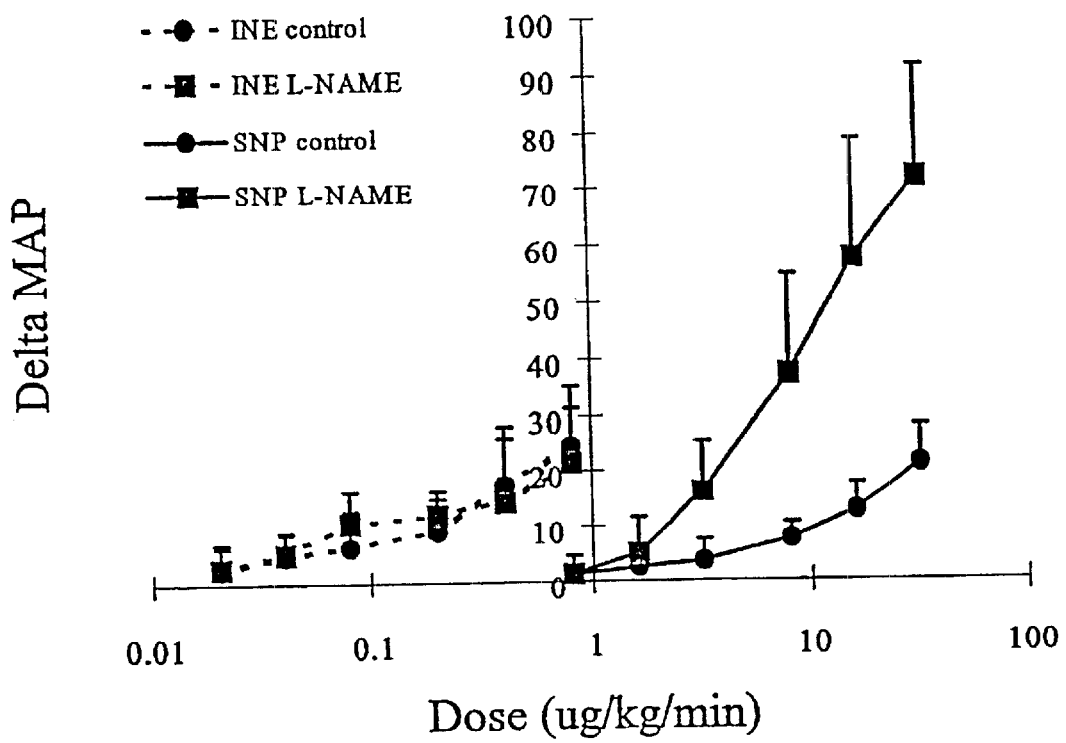
FIG. 8 is a graph comparing the sensitivity of mean arterial pressure to the NO donor sodium nitroprusside (SNP, right) and to isopropylnorepinephrine (INE, left), in the presence and absence of the NO synthase blocker L-NAME.
Figure 9:
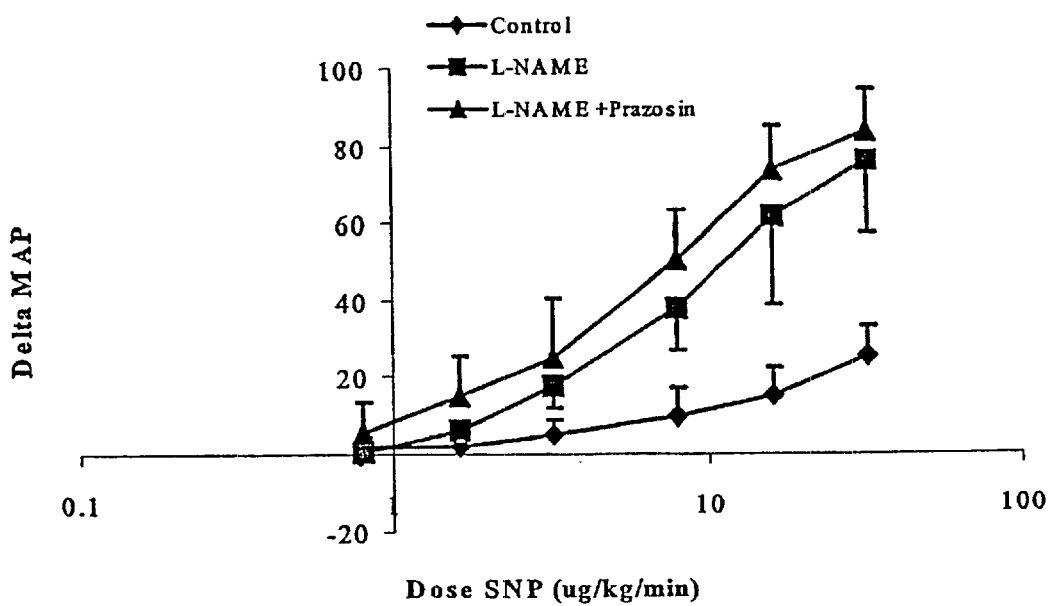
FIG. 9 is a cumulative dose response curve of mean arterial pressure to prazosin, an $\alpha_1$ blocker, in the presence and absence of NO synthase blockade (L-NAME).

FIGS. 8 and 9 provide more detailed information on the mechanism underlying the increased sensitivity of mean arterial pressure to NO following NO synthase blockade. As can be seen from FIGS. 8 and 9, neither of these two vasodilator agents was able to normalize the excessive vasoconstriction that follows NO blockade.

Specifically, the two curves on the left-hand side of FIG. 8 clearly demonstrate that the dose response of mean arterial pressure to INE is identical both before and after nitric oxide synthase blockade, indicating that the signal mediated by another vasodilator, INE, is unchanged in the presence or absence of nitric oxide. It is widely known that the mechanism of action of INE is via the activation of cAMP mediated signal transduction. In contrast the curves on the right-hand side of FIG. 8 indicate that there is an increase in sensitivity of mean arterial pressure to the NO donor SNP following the blockade of NO synthase.

From a mechanistic standpoint, INE causes vasodilation by the activation of the cAMP signal transduction system in the vasculature, whereas SNP causes vasodilation by the activation of the cGMP signal transduction system or by direct effects of NO (or an equivalent). The absence of a shift in sensitivity of mean arterial pressure to INE after NO blockade indicates that the increased sensitivity to NO donors such as SNP is independent of the cAMP signal transduction system, and may be directly dependent on the cGMP signal transduction system.

FIG. 9 illustrates that increased sensitivity to nitric oxide donors occurs following NO blockade, but does not occur following treatment with an $\alpha_1$ receptor antagonist (prazosin). As prazosin is a second vasodilator agent, similar to INE, these agents thus present two examples of different vasodilator mechanisms that do not influence the relationship between nitric oxide and endothelin, which relationship is in accordance with the methods of the present invention.

Therefore, to summarize the data presented in FIGS. 8 and 9, these data present examples demonstrating the relationship between nitric oxide and endothelin and the effects of a low-dose NO therapy on normalizing the affected circulation with respect to endothelin and maintaining and/or restoring vascular tone. These data also demonstrate that the imbalance in vascular tone that follows NO synthase blockade is not due to angiotensin II (data not shown), the sympathetic nervous system, or vasopressin (for example, via the $IP_3$ system), but is specific to the cGMP signal transduction system or direct effects of nitric oxide or its equivalent. The data further indicate that the addition of an $\alpha_1$ receptor antagonist, in contrast to an endothelin receptor antagonist, does not restore a normal level of vascular sensitivity. This is in accordance with the invention in that decreased levels of NO (via L-NAME) result in a marked up-regulation of endothelin, such as may be explained by an uncoupling of cGMP signalling.

Figure 10:
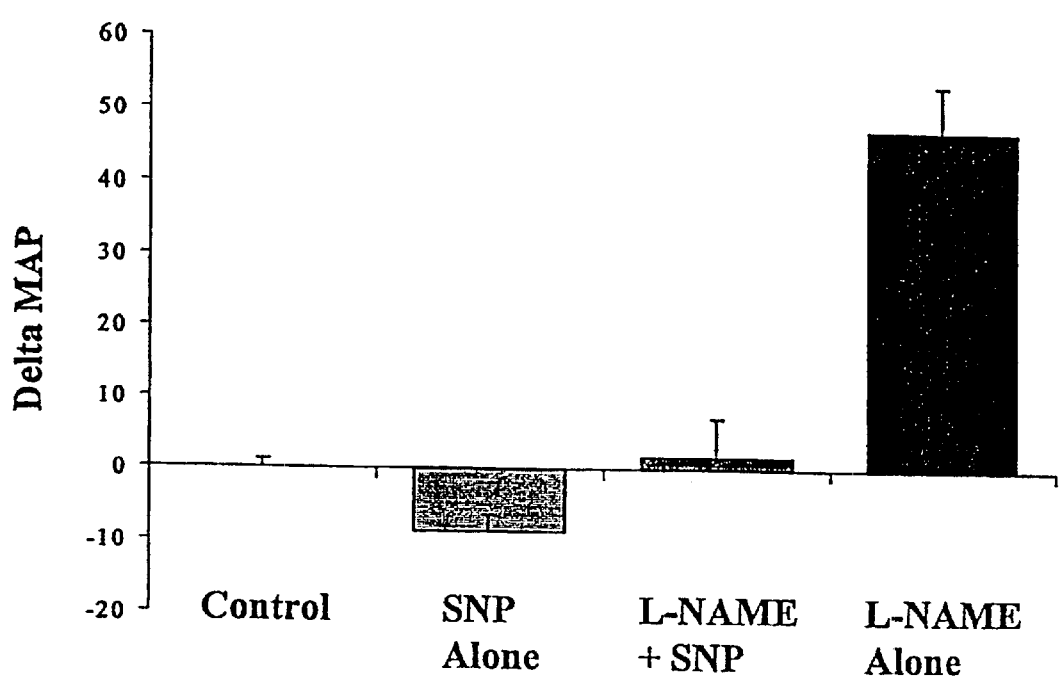
FIG. 10 is a graph illustrating a change in mean arterial pressure from control conditions in the presence of SNP low-dose, SNP+L-NAME, and L-NAME alone.
Figure 12:
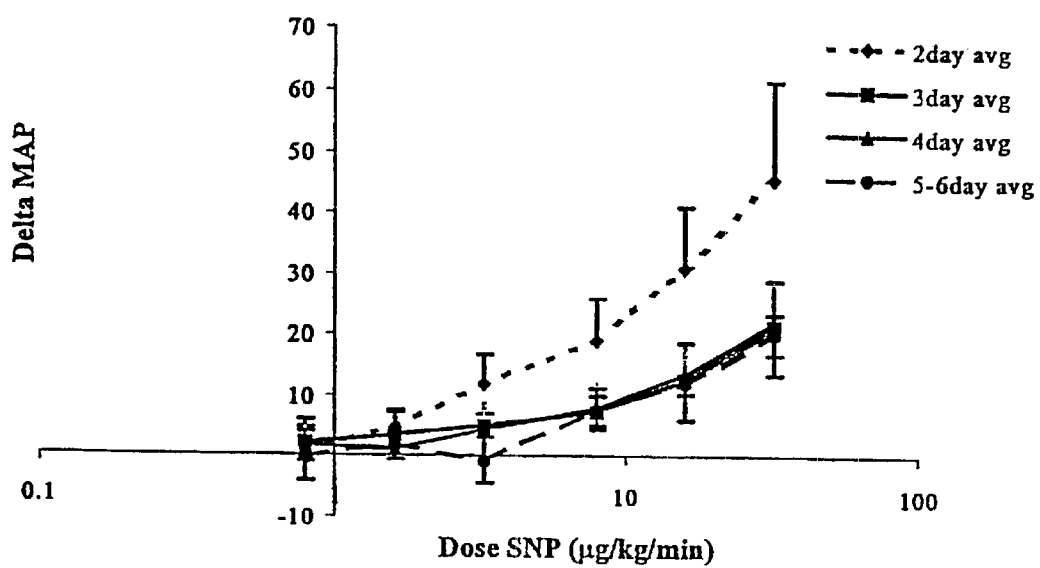

FIG. 10 is similar in principle to FIG. 2 and provides a further quantitation of the 'microdose' level of exogenous NO that maintains a normal level of vascular tone following nitric oxide synthase blockade with L-NAME. The graph of FIG. 10 illustrates that administering a level of SNP that lowers blood pressure by 8 mmHg completely prevents the development of hypertension following even maximal NO synthase blockade (which is usually 40 mmHg). Thus, in accordance with the invention, it can be seen that a microdose of SNP causes only a minimum level of vasodilation, but completely prevents the excessive vasoconstriction which occurs following high level NO synthase blockade using L-NAME.

Further evidence supports that nitric oxide chronically suppresses the effects of endothelin. As shown in FIG. 11, even normal levels of NO induce changes in the vasculature by countering the actions of endothelin. In FIG. 11 (top panel), there can be seen an increase in the sensitivity of mean arterial pressure to SNP following NO synthase blockade, and a decrease in the sensitivity to SNP in the presence of PD145065, an endothelin receptor antagonist. The rightward shift in the curve for PD145065 (under control conditions) clearly indicates that the response to NO by itself has been severely blunted. The bottom panel of FIG. 11 similarly indicates that the increased sensitivity to the NO donor GTN in response to treatment with L-NAME is abolished in the presence of PD145065. These results indicate that endothelin receptors are required to maintain the normal level of nitric oxide vasodilatory capacity under control conditions.

As would be apparent to a person of ordinary skill in the art, it is reasonable to use the rat as a model for the affected vascular systems discussed herein, such as, for example the pudendal and penis vasculature, and to extend such studies to appropriate dosages and therapies for other subjects, such as humans. As is evidenced by Mordenti, "Man versus Beast Pharmacokinetic Scaling in Mammals", *J. Pharm. Sci.* 75:1028–1040 (1986) and similar articles, dosage forms for animals, such as for example rats, can be and are widely used directly to establish dosage levels in human applications. One of the present inventors contributed to the development of a bioassay of erectile function in a rat model at least as early as 1991 (Heaton et al., *J. Urol.* 145:1099–1102, 1991), and also helped demonstrate in comparative tests of erectile function in humans and rats, that the narrow effective dose window of an orally administered drug, apomorphine, is almost identical when suitably adjusted for the differences in body weight as taught by Mordenti, cited above (Heaton et al., *Urology* 45:200–206, 1995).

Effect of NO in Renal Vasculature

In essence, the kidney functions as a reverse filter in that almost all of the contents of the blood are filtered into beginning "urine" of the kidney and the kidney specifically reabsorbs what it wants to retain later (in the nephrons and loop of Henle). A physical force, called the renal interstitial hydrostatic pressure (RIHP), in the tissues of the kidney can have a profound effect on this process. Increased RIHP presents a physical force opposing the reabsorption process affecting reabsorption of sodium, water and other parts of the beginning filtered urine. If not reabsorbed the result is a diuretic response (natriuresis). In cases of low RIHP the opposite occurs. Removal of the physical force opposing reabsorption results in volume accumulation (more blood volume=higher blood pressure). This pressure-mediated natriuresis is explained by the fact that some of the blood vessels in the kidney are not "auto regulated" (much like the penile vasculature), such that the pressure generated in the kidney tissue (RIHP) is dictated by the level of vasoconstriction/kidney perfusion. Excessive vasoconstriction results in a decrease in RIHP, thereby removing a strong mechanism by which the kidney prevents the reabsorption of the contents of filtered urine.

Figure 5:
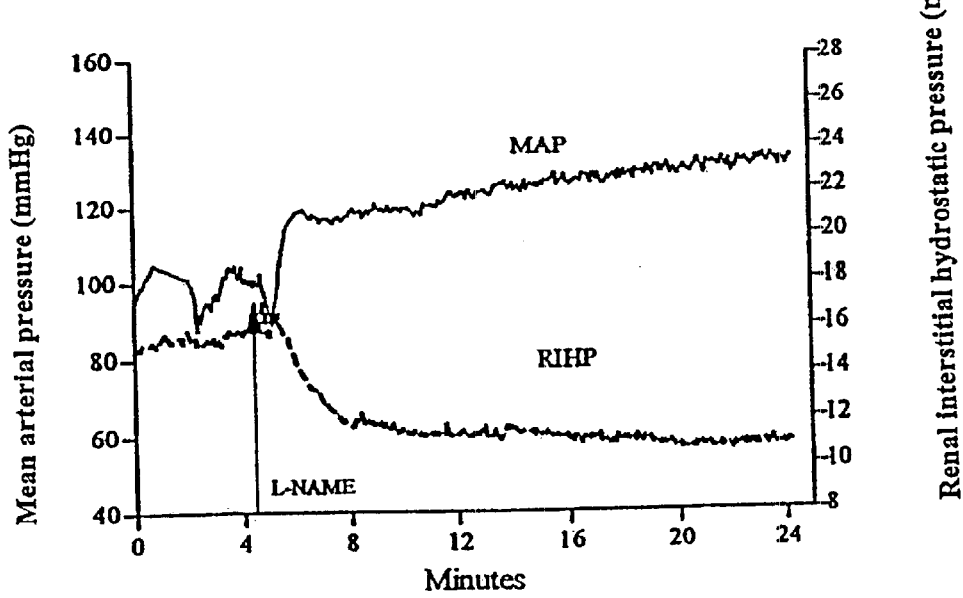
FIG. 5 is a representative tracing of changes in mean arterial pressure and renal interstitial hydrostatic pressure (RIHP) in respect of renal circulatory blockade of NO synthase.

It is possible to simulate a type of renal failure, where excessive vasoconstriction predominates. In these circumstances a volume conservation situation is created. This simulation is carried out by treatment of anaesthetized rats which are fitted with instrumentation for measuring RIHP and mean arterial blood pressure with NO synthase blockers (L-NAME). The results from such experiments are depicted in FIGS. 5, 6, and 7 which illustrate "raw" pressure tracings of an example of these preparations (Methods written below, see EXPERIMENTAL ASPECTS OF STUDIES REPORTED: Effects of NO in Renal Vasculature). The traces illustrate that administration of NO synthase blocker L-NAME, results in a sharp decline in RIHP (FIG. 5) consequent upon vasoconstriction of the vasculature. Administration of the NO precursor L-Arginine (150–200 mg/kg per min) reversed the renal vasoconstriction (as measured by RIHP changes—see FIG. 6) but did not alter the level of mean arterial pressure. When the L-Arginine administration is stopped (with continued administration of L-NAME, the RIHP once again sharply declines as illustrated in FIG. 7.

Clinical Data: For erectile dysfunction reversal with microdoses of NO General Methods. Measurements were made in a clinical erectile dysfunction (ED) laboratory in patients with previously diagnosed ED. These patients were being evaluated for the purpose of optimization of their intracernous injection dosing. All men were assessed using the Queen's University Human Sexuality Group Protocol (Kingston, Ontario, Canada).

Case 1

The first patient was a man with total erectile dysfunction of 18 months. History of hypertension, myocardial infarct (×2), coronary artery by-pass graft surgery, cerebral vascular accident and peripheral vascular disease. He was prescribed 0.2 mg/hr nitro patch (GTN, Ciba-Geigy) with no effect on systemic blood pressure. The therapy with 0.2 mg/hr nitro patch was on 2 occasions with 100% successful intercourse. He had angina on the second try. This result supports the view that the quantity of NO administered was working at a level significantly lower than quantities typically used.

Case 2

This patient was a man with no response to intra cavernosal injection therapy with conventional drugs. 0.2 mg/hr nitro patch (Ciba-Geigy) followed by 10 mcg PGE1. The patient experienced the first erection in 4 years (predating radical prostate surgery).

The concentration of glyceryl trinitrate (the typical form of NO donor derived from Nitrospray or Nitropatches) has been reported in the literature for such delivery routes to be in the order of 200 to 400 pg/ml of plasma (Sun et al., *J. Clin. Pharmacol.* 35:390, 1995). Based on the clinical case studies performed, it was noted that the beneficial effects of a 0.2 mg/h patch are observed after 20 to 30 minutes. This corresponds to a plasma concentration of 100 pg/ml. In respect of the application of the invention to ED therapy a preferred range of NO agent (such as GTN) is a steady state plasma concentration of about 50 to about 200 pg/ml. This range corresponds to the "window" referred to above as illustrated in FIG. 4.

Support for the proposal that the mechanism of action of the NO donors delivered at microdoses disclosed herein, are not directly vasodilatory, can be accomplished by giving animals NOS blocker high doses to create hypertension. This would be followed by infusion of an endothelin antagonist at a concentration which would almost completely reverse the hypertension induced by the NOS blocker. Subsequently, an NO donor, or combination of NO donors is infused. The concentration response curve from this infusion should now be similar to that obtained in control animals. In other words, the doses of NO which will cause a lowering of pressure will be at higher values, namely 10 to 24 times higher that in an L-NAME blocked animal alone thereby showing that high doses of NO are vasodilatory and lower ones are, on their own, not vasodilatory. Rather, they act to suppress ET.

While the routes of administration of the NO donors reported here include intracavernous (IC) injection of NO donor, or by nasal spray or by patch, the present invention includes administration by means of topical creams, pharmaceutically acceptable organic and inorganic carrier substances suitable for parenteral, enteral, intraurethral, vaginal application, or transmucosal application via, for example, the respiratory tract (e.g., by inhalation, such as through intranasal application), which do not deleteriously react with the active compounds.

Compositions of the invention are administered to subjects in a biologically compatible form suitable for pharmaceutical administration in vivo. By "biologically compatible form suitable for administration in vivo" is meant a form of the active compounds of the invention to be administered in which any toxic effects are outweighed by the therapeutic effects of the active compounds of the invention. The term subject is intended to include living organisms in which a response can be elicited, e.g., mammals. Examples of subjects include humans, dogs, cats, mice, rats, and transgenic species thereof.

Administration of a therapeutically active amount of the therapeutic compositions of the present invention is defined as an amount effective, at dosages and for periods of time necessary to achieve the desired result. For example, a therapeutically active amount of active compounds of the invention may vary according to factors such as the disease state, age, sex, and weight of the individual, and the ability of an agent or combination of agents of the invention to elicit a desired response in the individual. Dosage regimens may be adjusted to provide the optimum therapeutic response. For example, several divided doses may be administered or the dose may be proportionally reduced as indicated by the exigencies of the therapeutic situation.

The active compounds (e.g., SNP) may be administered in a convenient manner such as by injection (subcutaneous, intravenous, intracavernous, etc.), oral administration, inhalation, transdermal application, rectal administration, urethral administration, vaginal administration, or intracavernous introduction. Depending on the route of administration, the active compound or compounds may be coated in a material to protect the compound(s) from the action of enzymes, acids and other natural conditions which may inactivate the compound(s), or facilitate or enable delivery of said compound(s).

A SNP composition (or other NO donor) or as a separate agent can be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions and vehicles of solid, liquid or gas phase. To administer an agent or agents of the present invention by other than parenteral administration, it may be necessary to coat the active compound(s) of the invention with, or co-administer the agent or agents of the present invention with, a material to prevent its inactivation. Liposomes include water-in-oil-in-water emulsions as well as conventional liposomes (Strejan et al., *J. Neuroimmunol* 7:27 1984). The active compound(s) may also be administered parenterally or intraperitoneally. Dispersions can also be prepared in glycerol, liquid polyethylene glycols, and mixtures thereof in oils and other solutions. Under ordinary conditions of storage and use, these preparations may contain a preservative to prevent the growth of microorganisms, stability enhancers and compounds to preserve physical characteristics that are needed for appropriate delivery.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exits. It must be stable under the conditions of manufacture and storage and must be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, and sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., SNP) or compounds in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of an active ingredient of the invention plus any additional desired ingredient from a previously sterile-filtered solution thereof.

When an active compound(s) is suitably protected, as described above, the composition may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such medica and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the therapeutic treatment of individuals.

Experimental Aspects of Studies Reported

Quantitative Study

Animals

Male Sprague-Dawley rats (325 to 400 g) obtained from Charles River Laboratories (Montreal, Canada) were housed individually under conditions of 12-hour light/dark cycle, with room temperature at 22 to 24° C., and were provided with Purina rodent chow and tap water ad libitum for at least 2 days before any experiments were started.

Measurement of MAP and Short Acting Drug Administration

The surgical method was based on the technique of Thompson et al. (*Hypertens.* 20:809, 1992). In brief, rats were anaesthetized with ketamine/xylazine (70/5 mg/kg i.p.), and the descending aorta distal to the kidneys was catheterized with small bore Teflon tubing (0.012 in i.d., 30 gauge, Cole-Parmer, Laval, Quebec, Canada) inserted into vinyl tubing (0.02 in i.d., 0.060 in, 23 gauge). The inferior vena cava was also catheterized distal to the kidneys with small bore Teflon tubing (0.012 in i.d., 30 gauge, Cole-Parmer). The catheters were filled with heparinized saline (10 IU/ml) and held in place by a small amount of cyanoacrylate glue at the puncture site. The catheters were tunnelled subcutaneously and exteriorized at the back of the neck and sutured in place. Two days after surgery, MAP could be recorded (MacLab DAS, ADInstruments, Milford, Mass.). After connection, an equilibration period of approximately 30 minutes allowed for the determination of the steady state level of MAP before any recording began. Baseline MAP was determined from readings averaged over 5 minutes, taken from each rat at 15 minute intervals for at least 1 hour prior to the start of any experiment.

Sodium Nitroprusside and Glyceryl Trinitrate Concentration—Mean Arterial Pressure Response Curves Following Acute and Chronic $N^{\omega}$-nitro-L-arginine Methyl Ester Rats were randomly assigned treatment with $N^{\omega}$-nitro-L-arginine methyl ester (L-NAME) for 30 minutes (100 mg/kg, intraperitoneally) or 12 days (100 mg/kg, in drinking water) or tap water. Two days prior to the day of the experiment rats were instrumented with catheters, as described above. Following baseline measurements of MAP, rats were given a infusions of sodium nitroprusside (SNP, 0.5 to 32 ug/kg per minute dissolved in 0.9% sterile saline) with a step-wise increase in concentration every two minutes. Rats were allowed 30 minutes to recover from the SNP administration. Rats were then given infusions of glyceryl trinitrate (GTN, 0.5 to 32 ug/kg per minute dissolved in 0.9% sterile saline) with a step-wise increase in concentration every two minutes.

Throughout all of these pharmacological manipulations, MAP and HR were recorded at a sampling rate of 100 Hz and the data was stored on a disk drive for later analysis.

Effects of NO in Renal Vasculature

Surgical preparation: Experiments were performed in male Sprague-Dawley rates, 250 to 330 g, obtained from Charles River Laboratories (Montreal, Canada). Food (Purina rat chow) and water were provided ad libitum throughout the study. Rats were acclimatized for at least a week prior to experimentation in group housing under conditions of a 12-hour light/dark cycle, with room temperature at 22 to 24° C. 3 to 4 days prior to each experimental day, rats were instrumented with an aortic catheter as described in detail previously (Thompson et al., *Hypertens.*20:809, 1992). In brief, the rates were anaesthetized with ketamine hydrochloride (70 mg/kg i.p. (Rogarsetic, Rogar/STB Inc., Montreal, PQ) and xylazine hydrochloride (5 mg/kg i.p. (Rompum, Haver Inc., Etobickoe, ON) and placed on a heating pad to maintain a constant body temperature of 37° C. Additional ketamine was given, as necessary, during surgery. Following an abdominal incision, the descending aorta distal to the kidneys was catheterized with smallbore Teflon tubing (i.d.= 0.012 in, o.d.=0.030 in, 30 gauge, Cole-Parmer, Laval, Quebec, Canada), inserted into vinyl tubing (i.d.=0.02 in, o.d.=0.060 in, 23 gauge). The catheter was filled with heparinized saline (50 IU/ml, Grade 1-A Heparin Sodium salt, Sigma Chemical Co., St Louis) and held in place by a small amount of cyanoacrylate tissue glue (Lepage Ltd., Brampton, ON). The catheter was then flushed with a small volume (0.1–0.3 ml) of heparinized saline (50 IU/ml) and left entirely inside the abdominal cavity until the day of the RIHP measurements. The abdominal incision was sutured with 6-0 silk braided thread (Ethicon Ltd., Peterborough, Ontario). The rats were allowed to recover for 2 to 5 days, during which they were housed individually under the same conditions as described above. Rats were re-weighed following the recovery period and rats that had lost >30 g were considered to have not sufficiently recovered from the surgery and hence, were excluded from the study (Haskins, S. C., Postoperative care, In: Methods of Animal Experimentation, Vol. III Part A, eds. Gay et al. (Academic Press Inc., Orlando, 1986)).

Experimental Procedure: The RIHP measurements were carried out in rats anaesthetized with thiobutabarbital sodium (Inactin, 100 mg/kg i.p., Byk-Gulden, Constance, Germany). This anaesthetic is used most frequently by others for the study of RIHP and PN and, in preliminary studies, yielded similar results to those studies compared to a Ketamine/Xylazine anaesthetic preparation.

Rats were placed on a heating pad to maintain a constant body temperature of 37° C. and the abdominal incision was reopened. Hematocrits were determined by the microcapillary tube method from arterial blood samples (300 $\mu$l) obtained from the arterial catheter. Only rates in which the hematocrit was found to be between 40 and 45 percent were subsequently used. Rates with hematocrits out of this range were considered to be hemodynamically challenged due to the blood loss during surgery and, since reductions in hematocrit can compromise cardiovascular function, were not used in this study (Haskins, S. C., Postoperative care, In: Methods of Animal Experimentation, Vol. III Part A , eds. Gay et al. (Academic Press Inc., Orlando, 1986); Pirkle et al., *Endocrin.* 110:7, 1982; Houttuin et al., *Am J. Physiol.* 223:63, 1972).

The arterial catheter, inserted previously, was attached to a pressure transducer (model CDX3, Cobe), and the pulsatile signal recorded using a physiograph (Beckman, model R511 or MacLab, ADInstruments Pty Ltd., Castle Hill, Australia). Small sections of the aorta (<0.5 cm proximal to the right kidney), mesenteric and celiac arteries were isolated and silk ligatures were placed loosely around the vessels.

RIHP was measured by implanting a cannula into the lateral side of the left renal cortex (Garcia-Estañ et al., *Am. J. Physiol.*, 256:F63, 1989). The RIHP catheter was constructed by inserting a small core of porous polyethylene matrix material (2 mm, 35 $\mu$m pore size, Bel-Art Products, Pequannoc, N.J.) into the heat expanded end of a polyethylene catheter (PE-50, i.d.=0.023 in, o.d.=0.038 in×10–20 cm) such that approximately one-third of the matrix extends beyond the tubing. This technique ensures that tissue does not block the catheter while allowing for measurement of hydrostatic pressure (Roman et al., *Am. J. Physiol.* 248:F190, 1985; Ott et al., *J. Appl. Physiol.* 38:937, 1975). A 3 mm deep hole was made in the lateral surface of the left kidney with an electrocautery needle (26 gauge) and current was passed through the needle for approximately 3 to 5 seconds. Bleeding was completely stopped by applying soft pressure with a cotton swab. The kidney was kept dry before implanting the RIHP catheter. The RIHP catheter was inserted into the hole and then sealed to the surface of the kidney capsule with cyanoacrylate. The RIHP catheter was similarly attached to the physiograph via the pressure transducer. Lack of pulsatile pressure ensured that the catheter was not in a blood vessel. To further check the location of the catheter two procedures were performed: (i) a small volume (100–200 μl) of saline (10 IU/ml heparin) was slowly infused in order to obtain a characteristic increase in RIHP (Ott et al., 1975) and (ii) a RIHP response to renal vein occlusion (RVO) was observed (Garcia-Estañ et al., *Am. J. Physiol.*, 256:F63, 1989). Rats that failed to show these characteristic responses (FIG. 2-1) were excluded from the experiment After a 10 to 15 minute equilibration period, the RVO response from the RIHP catheter and a pulsatile recording from the arterial catheter were re-confirmed and a baseline MAP and RIHP were recorded. During the control periods of the experiment, the exposed abdominal cavity was kept moist by covering with a wet gauze patch and 0.9% saline. In each experiment, arterial pressure was manipulated systematically from low to high MAP by sequentially tightening the ligatures around the upper aorta, celiac artery and mesenteric artery. Pressure changes were initially maintained for approximately 5 to 7 minutes in order to ensure that both MAP and RIHP equilibrate to the new steady state. As it was determined that RIHP equilibrated in less than 3 minutes all date was collected within this time. The RVO-RIHP response was checked periodically after reaching different arterial pressures. This sequence of arterial pressure manipulations was repeated after a 10 to 15 minute control period at baseline MAP and RIHP. The position of the RIHP catheter was verified at the end of each experiment and was typically found in the corticomedullary junction.

Those skilled in the art will recognize, or be able to ascertain through routine experimentation, equivalents to the specific embodiments described herein. Such equivalents are considered to be within the scope of the invention and are covered by the appended claims.

We claim:

1. A method for treating a urogenital disorder in a female subject, said method comprising:

administering to said female subject an agent that enhances NO while maintaining normal systemic vascular tone, to treat said urogenital disorder in said female subject.

2. The method for treating a urogenital disorder of claim 1, wherein said urogenital disorder is selected from the group consisting of decreased vaginal lubrication, decreased vaginal engorgement, pain during intercourse, dyspareunia, urogenital infections, effects on urogenitalia due to postmenopause or diabetes, vascular disease, estrogen depletion conditions, sexual dysfunction, and idiosyncratic vaginal dryness.

3. The method for treating a urogenital disorder of claim 2, wherein said urogenital disorder is selected from the group consisting of decreased vaginal engorgement, pain during intercourse and dyspareunia.

4. The method for treating a urogenital disorder of claim 3, wherein said urogenital disorder is dyspareunia.

5. The method for treating a urogenital disorder of claim 1, wherein said administration of said agent is selected from the group consisting of oral, sublingual, buccal, intravenous, transdermal, vaginal, rectal, by inhalation, enteral, and parental.

6. The method for treating a urogenital disorder of claim 1, wherein administration of said agent is at concentration that is about ½ to about ¹⁄₂₀ of a concentration of said agent required to induce vasodilation in a healthy vasculature.

7. The method for treating a urogenital disorder of claim 6, wherein administration of said agent is at concentration that is about ¼ to about ¹⁄₂₀ of a concentration of said agent required to induce vasodilation in healthy vasculature.

8. The method for treating a urogenital disorder of claim 7, wherein administration of said agent is at concentration that is about ⅛ to about ¹⁄₁₆ of a concentration of said agent required to induce vasodilation in healthy vasculature.

9. The method for treating a urogenital disorder of claim 1, wherein said agent which enhances NO is GTN, and said level of administration is a plasma concentration below about 250 pg/ml of GTN.

10. The method for treating a urogenital disorder of claim 1, wherein said agent is selected from the group consisting of NO, CO. NO donors, CO donors, activators of guanylyl cyclase, PDE inhibitors, and substances which produce an effect equivalent to that of NO.

11. The method for treating a urogenital disorder of claim 10, wherein said agent is a PDE inhibitor.

12. The method for treating a urogenital disorder of claim 10, wherein said NO donor is selected from the group consisting of glyceryl trinitrate, isosorbide 5-mononitrate, isosorbide dinitrate, pentaerythritol tetranitrate, erythrityl tetranitrate, sodium nitroprusside, 3-morpholinosydnonimine molsidomine, S-nitroso-N-acetylpenicillamine, S-nitrosoglutathione, and N-hydroxy-L-arginine.

13. The method for treating a urogenital disorder of claim 12, wherein said NO donor is glyceryl trinitrate (GTN).

14. A method for improving blood flow to the vagina, said method comprising: administering to a female subject an agent that enhances NO while maintaining normal systemic vascular tone, to improve blood flow to the vagina.

15. A method for treating dyspareunia in a female subject, said method comprising: administering to said female subject an agent that enhances NO while maintaining normal systemic vascular tone, to treat dyspareunia in said female subject.

16. A method for treating a urogenital disorder in a female subject, said method comprising: topically administering to said female subject an agent that enhances NO while maintaining normal systemic vascular tone, to treat said urogenital disorder in said female subject.

17. A method for restoring NO/ET balance in a female subject, said method comprising: administering to said female subject an agent that enhances NO while maintaining normal systemic vascular tone, to restore NO/ET balance in said female subject.

18. A method for treating an estrogen depletion condition in a female subject, said method comprising: administering to said female subject an agent that enhances NO while maintaining normal systemic vascular tone, to treat said estrogen depletion condition in said female subject.

19. A method for improving vaginal blood flow in a female subject, said method comprising: administering to said female subject an agent that enhances NO while maintaining normal systemic vascular tone, to improve vaginal blood flow in said female subject.

20. A method for improving vaginal lubrication in a female subject, said method comprising: administering to said female subject an agent that enhances NO while maintaining normal systemic vascular tone, to improve vaginal lubrication in said female subject.

* * * * *